United States Patent [19]

Holtkamp, Sr.

[11] Patent Number: Plant 7,109

[45] Date of Patent: Jan. 16, 1990

[54] AFRICAN VIOLET PLANT NAMED IMPROVED TEXAS

[76] Inventor: Reinhold Holtkamp, Sr., Werther Strasse 112, D4294 Isselburg, Fed. Rep. of Germany

[21] Appl. No.: 310,759

[22] Filed: Feb. 15, 1989

[51] Int. Cl.[4] ..... A01H 5/00
[52] U.S. Cl. ..... Plt./69
[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Improved Texas characterized by its single violet-shaped, blue flowers with frilled edges and somewhat darker center; strong, upright flower stems that curve slightly toward the center to form a compact bouquet above the leaves; relatively dark green, oval to heart-shaped leaves; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Improved Texas.

The new cultivar was referred to during the breeding and selection process by the designation H 90/3 and is a product of a planned breeding program. The basic objective of the breeding program was to create a new African violet cultivar improving certain characteristics of the cultivar Texas, disclosed in my U.S. Plant Pat. No. 4,776, granted Oct. 31, 1981. The new cultivar was originated from a cross made by me in the controlled breeding program in Haffen, Federal Republic of Germany. The female, or seed parent was a cultivar designated E 29/7. The male, or pollen parent was a cultivar designated d 198/5.

Improved Texas was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Improved Texas has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn. under greenhouse conditions which closely approximate those generally used in commercial practice.

The following traits have been repeatedly observed and are determined to be basic characteristics of Improved Texas, which in combination distinguish this African violet as a new and distinct cultivar.

(1) Strong, upright flower stems curving slightly toward the center.

(2) Single violet-shaped, blue flowers with frilled edges.

(3) Each plant carries 6–7 and more upright flower stems each of which carries 8–10 and more flowers.

(4) Long lasting, non-dropping flowers.

(5) Vigorous and compact grower.

(6) Plant saleable 10 to 11 weeks after potting.

(7) Seed capsules push slightly through.

(8) Oval to heart-shaped, relatively dark green leaves.

(9) After maturity the flowers dry off, and remain on the peduncle without becoming infected by botrytis.

The new cultivar is most similar to, and was specifically intended to improve upon the characteristics of, my previously patented cultivar Texas. In comparison to Texas, the new cultivar is principally distiniguished by its smaller flowers, more compact growth habit, and by its longer flowering period.

The accompanying color photographic drawing shows a typical specimen plant of the new cultivar. The colors appearing in the photograph are as true as possible with color illustrations of this type.

In the following description, color references are made to the Royal Horticultural Society Colour Chart (RHS), except where general colors of ordinary significance are referred to. Color values were taken under natural sunlight conditions at approximately 1 p.m. in Nashville, Tenn.

Botanical classification: *Saintpaulia ionantha,* Ramat., c.v. Improved Texas.

Parentage:

*Male parent.*—d 198/5.

*Female parent.*—E 29/7.

Propagation: The new cultivar holds its distinguishing characteristics through successive propagations by leaf cuttings.

Plant: From 8 cm to 11 cm tall when grown in pots, and approximately 22–25 cm in diameter when fully grown.

*Leaves.*—General form: Oval to heart-shaped. Diameter: 60–75 mm. Texture: Leatherlike. Aspect: Hairy, slightly shiny. Veins: Upperside: well visible; underside: very well pronounced, light green, occasionally purplish red touch, shiny. Color (upperside): Yellow-Green Group 147 A. Color (underside): Greyed-Green Group 194 D with touch of Greyed-Purple Group 186 A. Petiole: Strong upright, purplish red, hairy.

*Flowers.*—Buds: Ball-shaped, 8–9 mm just before opening, purplish blue. Sepals: Five (5). Color: Brownish. Calyx: Shape: Funnel-shaped. Aspect: Spear-shaped, hairy. Peduncle: Character:

Strong upright, hairy. Color: Purplish brown. Individual flowers: Size: 35–40 mm. Shape: Single violet-shaped (3 large, 2 small petals) with frilled edges. Color (upperside): Violet-Blue Group 93 A to B. Under cooler temperatures and more intensive lighting, the blue tends to intensify. Color (underside): Violet-Blue Group 88 B to C. Borne: Each flower stem carries 8–10 and more flowers on strong, upright peduncle that are free standing above the leaves, thereby forming a compact bouquet. Flowering habit: Flowers 10–11 weeks after potting.

*Reproductive organs.*—Stamens: Two (2). Anthers: 2 composed of 4 anther cells, seed capsule pushes slightly through. Filaments: Yellowish green with purplish blue on edge, 4 mm long. Pollen color: Yellow Group 7 A. Styles: 7 mm long, purplish blue, base of ovary light green and hairy.

*Roots.*—Normally developed, white when young, turning slightly brownish when older.

Disease resistance: Good.

General observations: Improved Texas is a very attractive, vigorous and compact grower with relatively dark green, oval to heart-shaped leaves. A tight bouquet of flowers free standing above the leaves develops after approximately 10–11 weeks. Each of the 6–7 and more strong flower stems carries 8–10 and more single violet-shaped, frilled blue flowers contrasting nicely with the bright yellow anthers. The color at the center of the blooms is somewhat darker. Occasionally, an additional small petal may develop. The flowers are long-lasting and non-dropping.

I claim:

1. A new and distinct cultivar of African violet named Improved Texas, as described and illustrated, and particularly characterized by its single violet-shaped, blue flowers with frilled edges and somewhat darker center; strong, upright flower stems that curve slightly toward the center to form a compact bouquet above the leaves; relatively dark green, oval to heart-shaped leaves; profuse flowering, vigorous and compact growth habit, flowering 10–11 weeks after potting, and its long lasting and non-dropping flowers.

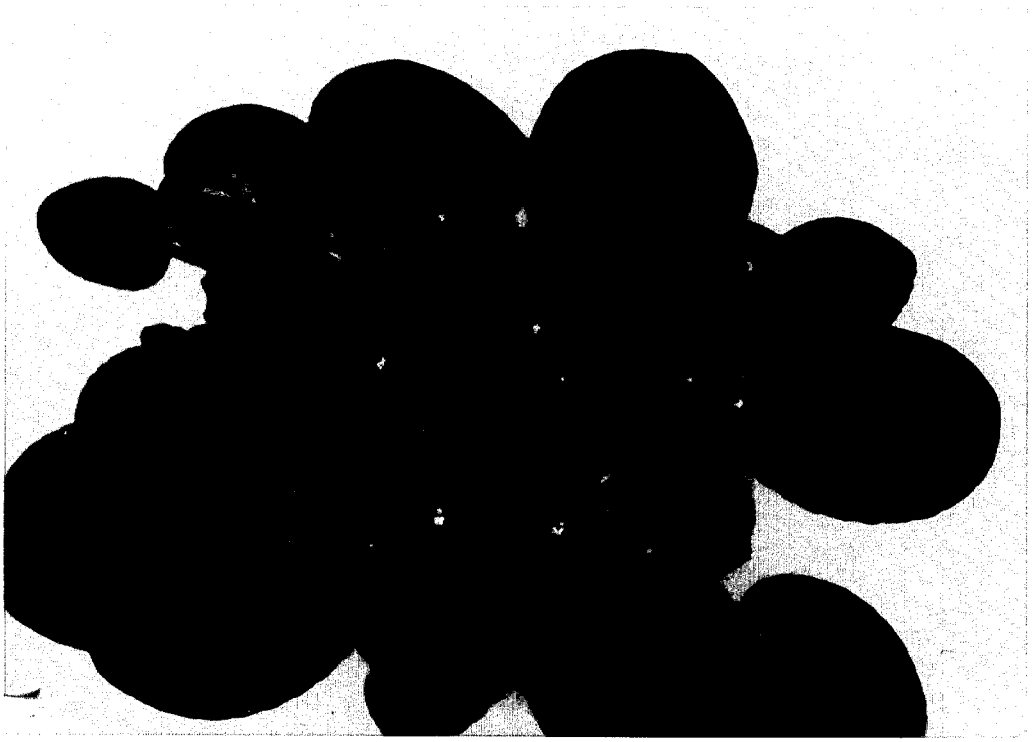

* * * * *